United States Patent [19]
Sobel et al.

[11] Patent Number: 6,135,272
[45] Date of Patent: Oct. 24, 2000

[54] PACKAGE FOR SUTURES

[75] Inventors: Martin Sobel, Flemington; Konstantin Ivanov, Bound Brook; Marvin Alpern, Glen Ridge; Clifford Dey, Flemington; Joseph Stanley Siernos, Whitehouse Station; William F. Smith, Ringoes, all of N.J.

[73] Assignee: Ethicon, Inc., Somerville, N.J.

[21] Appl. No.: 09/425,486

[22] Filed: Oct. 22, 1999

[51] Int. Cl.[7] .................................................. A61B 17/06
[52] U.S. Cl. ......................................... 206/63.3; 206/380
[58] Field of Search .................................. 206/63.3, 225, 206/388, 478, 480, 482, 227, 380

[56] References Cited

U.S. PATENT DOCUMENTS

| | | | |
|---|---|---|---|
| 5,179,818 | 1/1993 | Kalinski et al. | 53/430 |
| 5,271,495 | 12/1993 | Alpern | 206/63.3 |
| 5,284,240 | 2/1994 | Alpern et al. | 206/63.3 |
| 5,655,652 | 8/1997 | Sobel et al. | 206/63.3 |
| 5,906,273 | 5/1999 | Pohle et al. | 206/63.3 |
| 6,016,905 | 1/2000 | Gemma et al. | 206/63.3 |
| 6,047,815 | 4/2000 | Cerwin et al. | 206/63.3 |

*Primary Examiner*—David T. Fidei
*Attorney, Agent, or Firm*—Emil Richard Skula

[57] ABSTRACT

A package for sutures having a winding channel. The package has a base member and a cover member that is mounted to the base member. A plurality of cantilevered doors cover the winding channel.

16 Claims, 11 Drawing Sheets

PACKAGE FOR SUTURES

TECHNICAL FIELD

The field of art to which this invention pertains is packaging, in particular, packages used for surgical sutures suitable for high-speed automatic packaging machinery.

BACKGROUND OF THE INVENTION

Packaging for surgical sutures and needles is well known in the art. Conventional surgical suture and needles packages serve several useful functions, including protecting the needles and sutures during handling, shipping, and storage. In addition, the packages facilitate access and release of the needles and sutures during surgery or other medical procedures prior to application. The packages may be used for surgical sutures armed with surgical needles or for unarmed surgical sutures without needles. There are two types of packages that have been conventionally used for surgical needles and sutures. One type of package is a paper folder package wherein a medical grade paperboard is folded and cut into a plurality of panels. The suture is then wound onto a panel, and the package is then assembled by first folding the panels into a desired configuration, and then locking the panels in place using slits and locking tabs which have been cut into the panels. Another type of suture package which has been used is a tray package having a winding channel. These tray packages typically have an oval shape with outer and inner walls forming an oval winding channel. The packages are typically molded from plastics. The packages are mounted onto a winding fixture and sutures are then wound into the winding channel. Suture packages typically have a needle park member for mounting and securing a surgical needle if a surgical needle is mounted to the sutures. Conventional needle parks can consist of foam members, or equivalent retention structures. The needle park members can also be utilized for mounting one end of a suture wound into the winding channel. U.S. Pat. No. 4,961,498 discloses a two-piece suture package having an oval winding channel. U.S. Pat. No. 4,967,902 discloses a one-piece channel suture package having a plurality of door members which retain the suture in the channel. U.S. Pat. No. 5,230,424 discloses a package having a substantially square shape and having a square shaped suture channel wherein a plurality of cantilevered doors are mounted to an inner wall to maintain sutures in the channel. U.S. Pat. No. 5,665,652 discloses a package having an oval-shaped winding channel with a top friction plate member in lieu of doors or cantilevered doors. U.S. Pat. No. 5,131,533 discloses a needle park having a hinged section. U.S. Pat. No. 5,180,053 discloses a suture package having a cantilevered arm needle park.

Although the suture tray packages of the prior art are adequate and effective for their intended use. There are disadvantages associated with such packages. An example of one type of problem which may occur is suture "hang-up" when the surgeon attempts to withdraw the suture from the package. Accordingly, there is a need in this art for novel suture tray packages having winding channels which are readily adaptable to high-speed packaging processes which overcome the disadvantages of the prior art packages, including problems associated with suture withdrawal.

DISCLOSURE OF THE INVENTION

Therefore, it is an object of the present invention to provide a novel tray package having a winding channel which is useful in a high-speed packaging process for packaging surgical sutures.

It is also an object of the present invention to provide a tray package with the ability to securely maintain sutures in a channel.

It is still yet a further object of the present invention to provide a novel suture tray package which facilitates withdrawal of sutures from the package.

Accordingly, a suture package is disclosed. The package has a base member having a top, a bottom and an outer periphery and a longitudinal axis. An outer wall extends upwardly about the periphery of said base member, said outer wall having an inner surface, an outer surface, and a top. A plurality of standoff members extend radially inward from the inner surface of the outer onto at least part of the top surface of the base member. A plurality of fastener receiving holes extend through the base member. An optional annular recess surrounds each fastener receiving hole on the bottom of the base member. A plurality of tab receiving openings are contained in the base member. A plurality of locating pin receiving holes also extend through the base member. A lifting tab receiving hole extends through the base member.

There is also a suture channel cover member for mounting to the base member. The suture channel cover member has a top, a bottom and an outer periphery. A plurality of fastener members extend downwardly from the bottom of the cover member. An inner track wall extends upwardly from the outer periphery of the cover member, said inner track wall has an inner side, an outer side and a top. A plurality of cantilevered cover door members extend radially outward from the outer track wall. Each door member has a top surface, a bottom surface, an inner hinged end and an outer end. The door members have a first notched opening centrally located in the outer end extending partially into each door member. The door members are separated from each by spaces. Each door member has a second notched opening in the end adjacent to one side next to a separation space. A rim member extends downwardly from the outer end of each door member, the rim member has a bottom, opposed, ends and an inner surface and an outer surface. A port exit opening having a first end and a second end is located in the outer track wall and forms a suture port. A curved exit port arm is adjacent to a first end of the exit port, said port arm extends upwardly from the top surface of the base member from the track wall to a point on the base member interior to the track wall. A ramp member is located on the base member adjacent to the second end of the port opening. A suture park member extends up from the top surface of the cover member. A slit in the base member interior to the track wall forms the tab lifting member. The cover member is mounted to the base member to form the package of the present invention by aligning the cover member with the base member and inserting the fasteners and pin members of the cover into the fastener receiving holes of the base member such that the bottoms of the rim member rest upon the surface of the base member, and the bottom of the rim member of each cover member rests upon the top of the base member. This forms a suture channel between the outer side of the track wall, the top of the base member, the inner side of the rim member and the bottom of the door members. An optional paper top cover may be mounted to the assembled package.

These and other features and advantages of the present invention will become more apparent from the following description and accompanying drawings.

DESCRIPTION OF THE PREFERRED EMBODIMENTS

The package 10 of the present invention is illustrated in FIGS. 1–13. As seen in FIGS. 1, 2, 3, 5 and 10, the package 10 has base member 30, suture channel cover member 200, and optional package cover 400. Referring now in more detail to also to FIGS. 10 and 12, the base member 30 is seen to have top side 31 and bottom side 32. Base member 30 is also seen to have outer periphery 35. The base member 30 is seen to be a substantially flat substantially oval shaped member having a longitudinal axis 34. However, although it is desired that the base member 30 along with the package 10 be oval shaped, other configurations can be used including circular, polygonal, square with rounded corners, and the like and combinations thereof and equivalents thereof. Extending upwardly about the periphery 35 of base member 30 is the outer wall 40. Outer wall 40 is seen to have bottom 41, inner side 42, outer side 43 and top 44. The standoff members 60 are seen to extend inwardly from the inner side 42 of the outer wall 40 onto the top side 31 of base member 30. Standoff members 60 are seen to have bottoms 64 and flat tops 62. The tops 62 of members 60 are preferably below the top 44 of wall 40. The standoff members 60 are seen to preferably have substantially curved outer end surfaces 66, and may also have flat outer end surfaces 68, or combinations of members 60 with flat and curved outer surfaces. If desired, the standoff members 60 may have other configurations for end surfaces including semi-circular, polygonal, oval, triangular, combinations thereof and equivalents thereof and the like.

Figure 6:
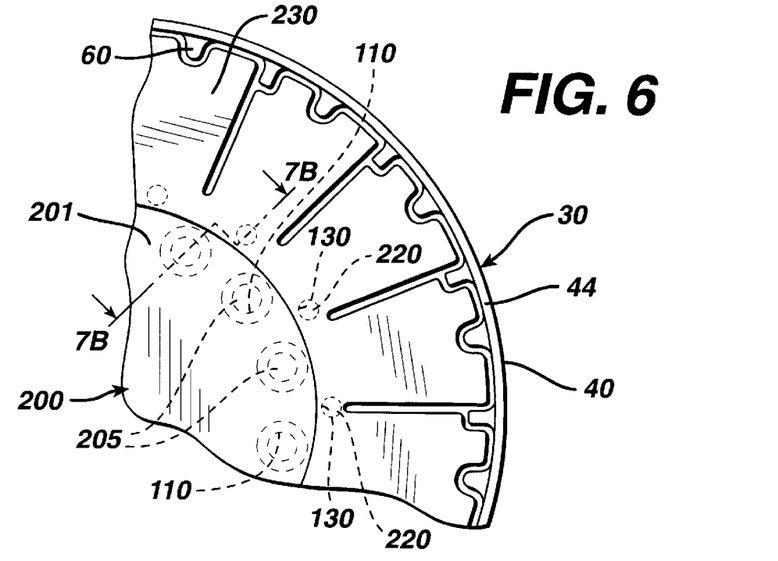
FIG. 6 is a partial, magnified section of the package of FIG. 5 illustrating the cantilevered door members, and the position of rivets in relation to the mounting pins.
Figure 10:
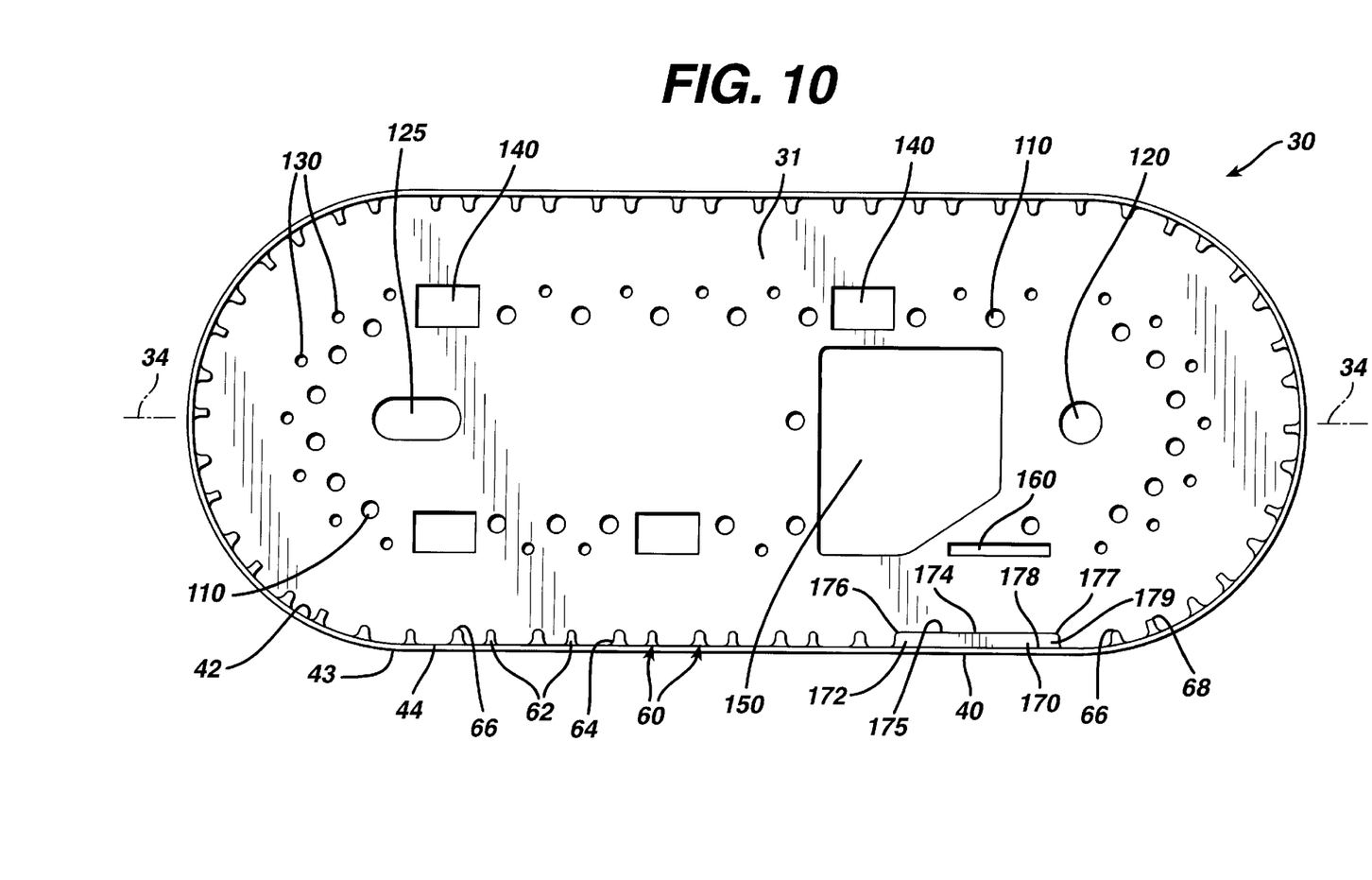
FIG. 10 is a top view of the base member of the package of the present invention.
Figure 12:
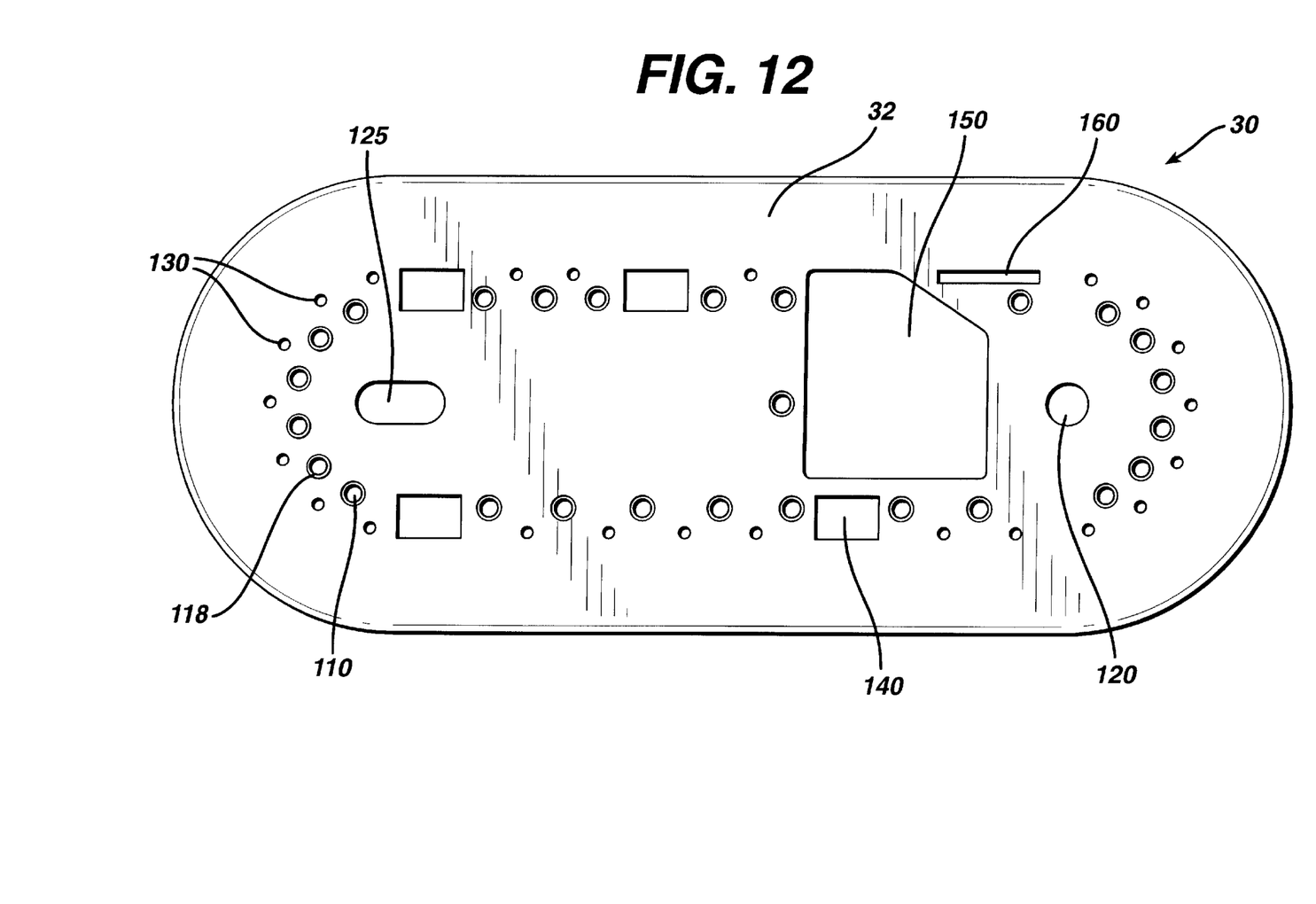
FIG. 12 is a bottom view of the base member of the present invention.
Figure 13:
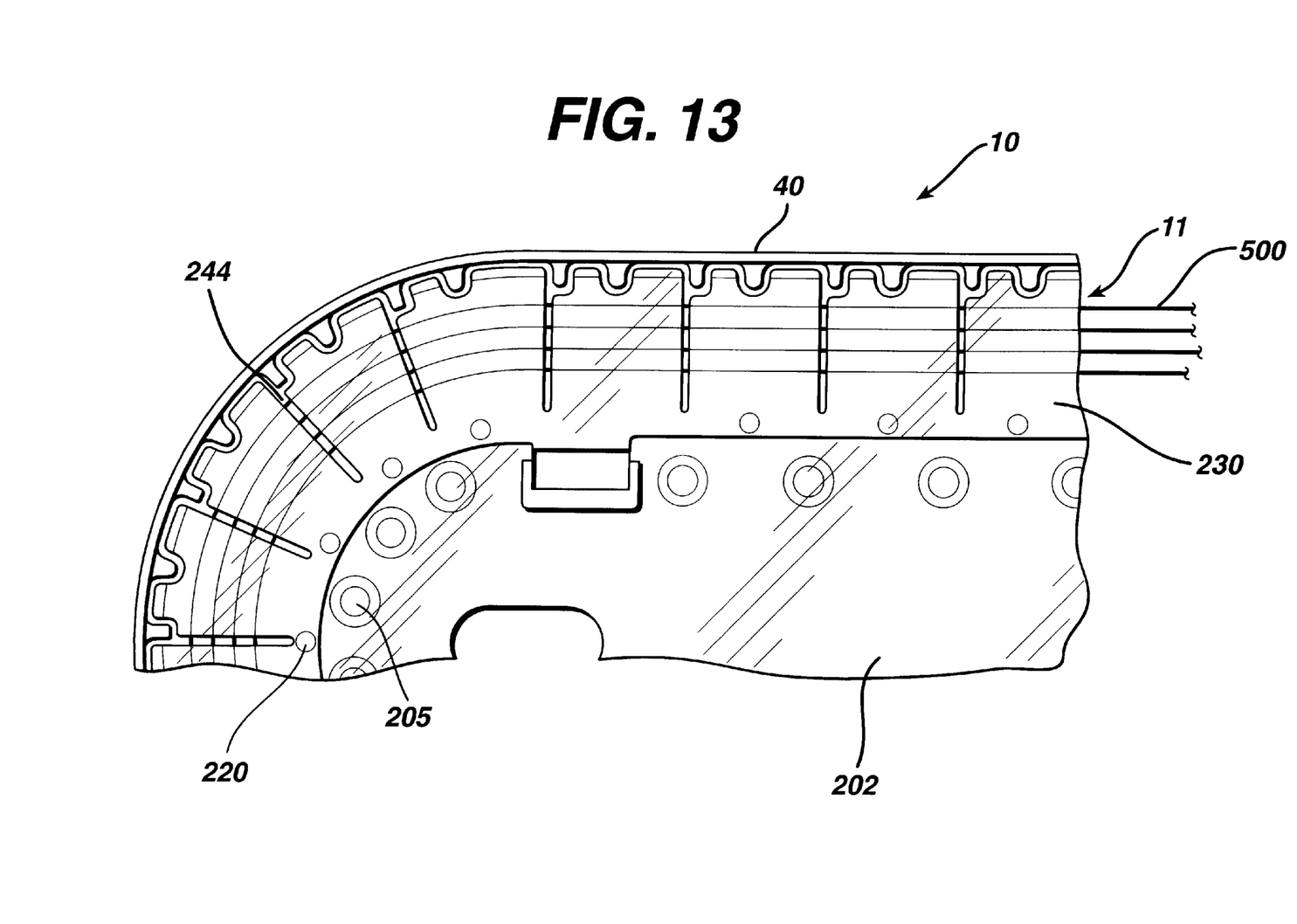
FIG. 13 is a magnified, partial top view section of an assembled package of the present invention having multiple loops of suture contained in the suture channel.

Extending through the bottom of the base member 30 are a plurality of rivet retention holes 110. The rivet retention holes 110 are seen to be circular holes extending through the base member 30. Referring to FIGS. 10 and 12, it can be seen that on the bottom 32 of the base member 30, each rivet retention hole 110 is surrounded by an annular space 118 to facilitate spreading of the bottom of a rivet. Also extending through the base member 30, are the circular winding pin locating hole 120 and the oval pin locating hole 125. The holes 120 and 125 are seen to be disposed along longitudinal axis 34 and are at opposite ends of the base member 30. Also seen to extend through the base member 30 are the locating pin retention holes 130. Locating pin retention holes 130 are seen to be located between wall 40 and rivet holes 110. The holes 130 are preferably arrayed such that there is a pin hole between every two adjacent rivet holes 110 as seen in FIG. 6. The cover cleat retention holes 140 are also seen to extend through the base member 30. The holes are seen to be substantially rectangularly shaped, however, the holes may have any shape suitable for receiving the cleats on paper cover 400 as described herein below. The lifting tab receiving opening 150 is seen to be located in base member 30 toward circular locating hole 120. Also extending through base member 30 adjacent to opening 150 is the rectangular opening 160 for receiving suture port tab member 290. Extending inwardly from the inner side 42 of outer wall 40 and up from top side 31 is the suture port wall 170 having top 172, bottom 174 and inner surface 175, and ends 176 and 177. Adjacent to end 177 is notch 178 creating support surface 179. Inner surface 175 may be flat or curved or have other geometric shapes and combinations thereof.

Figure 1:
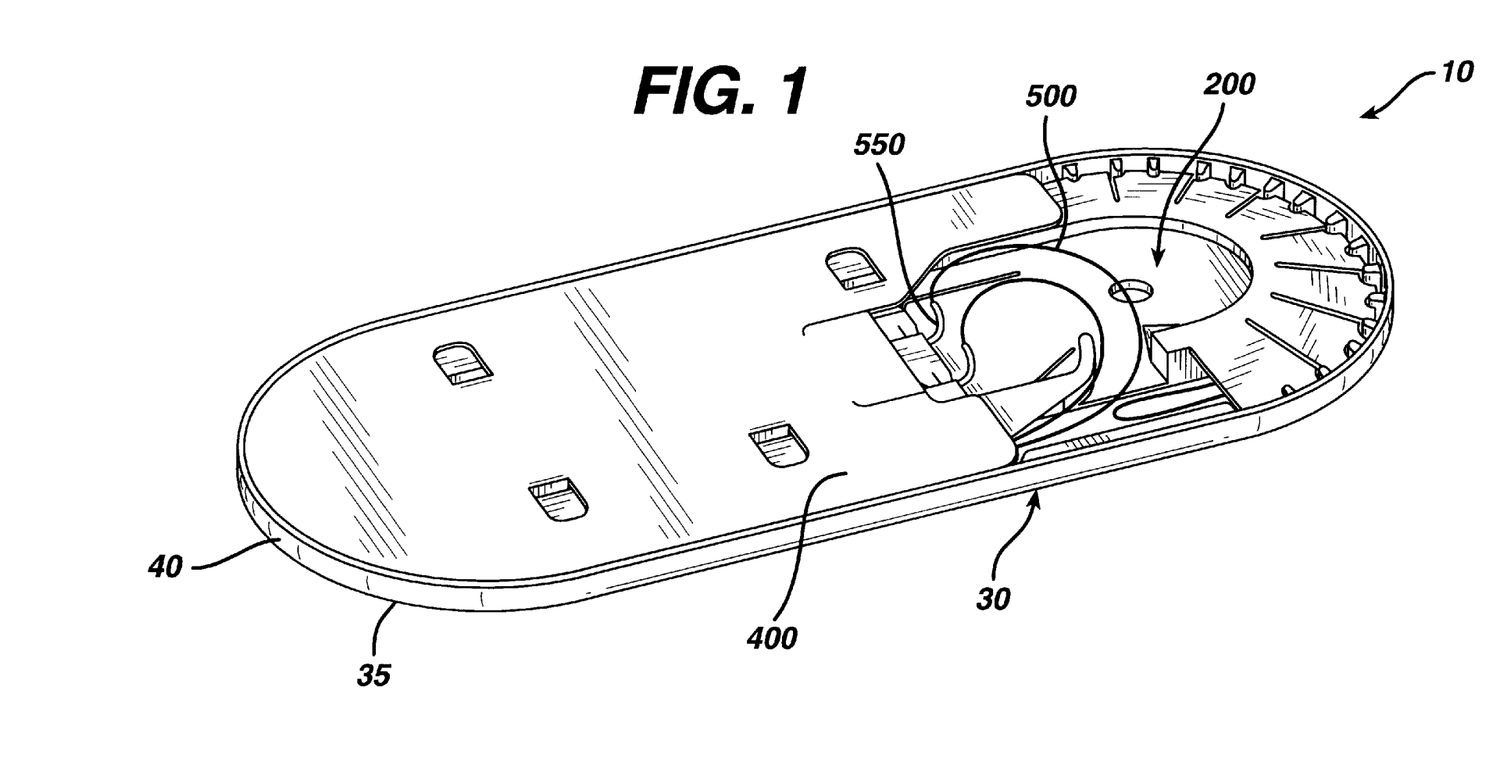
FIG. 1 is a perspective view of a package of the present invention having surgical sutures and attached needles mounted therein, and having a paper cover mounted thereto.
Figure 2:
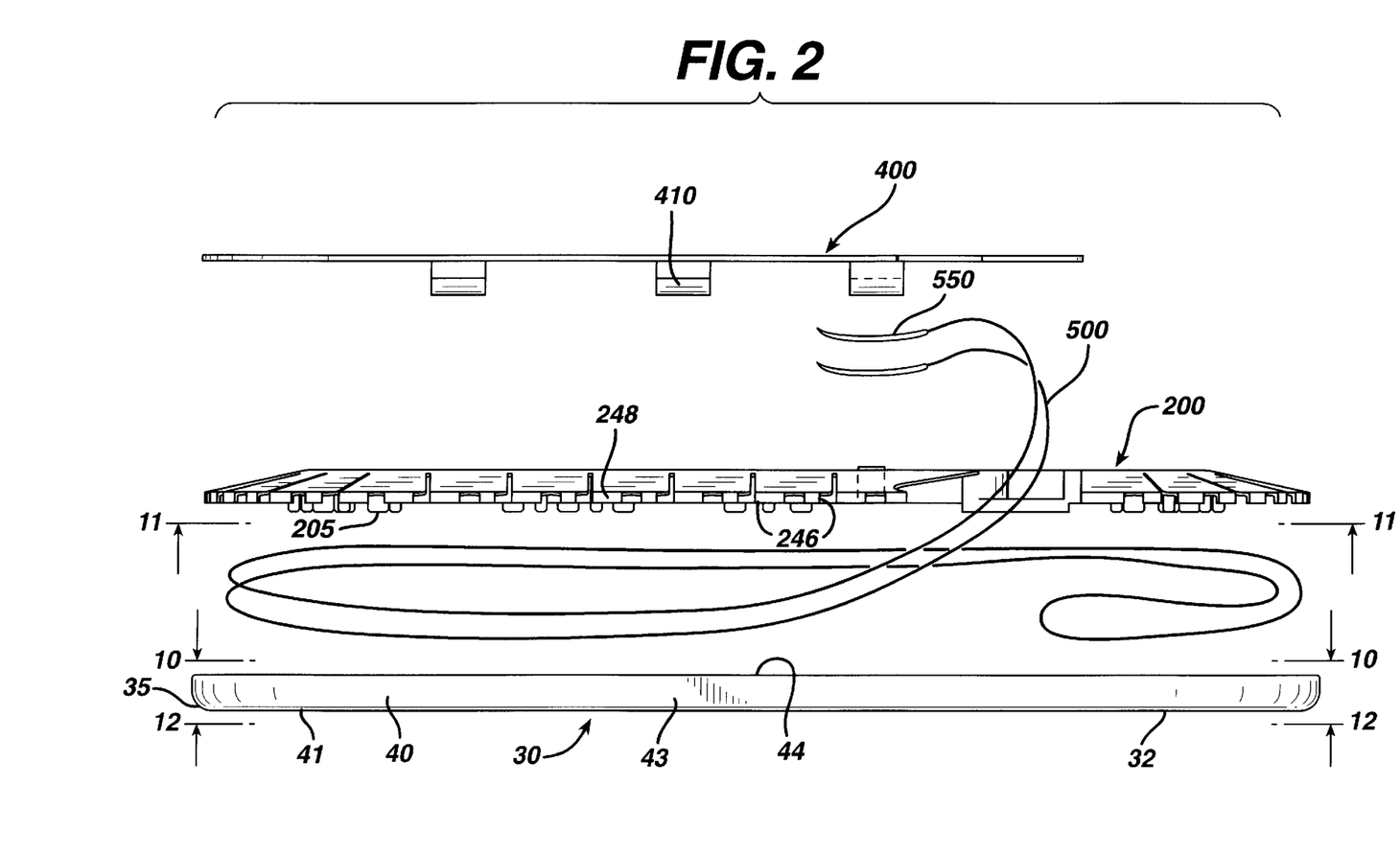
FIG. 2 is an exploded side view of the package of FIG. 1.
Figure 3:
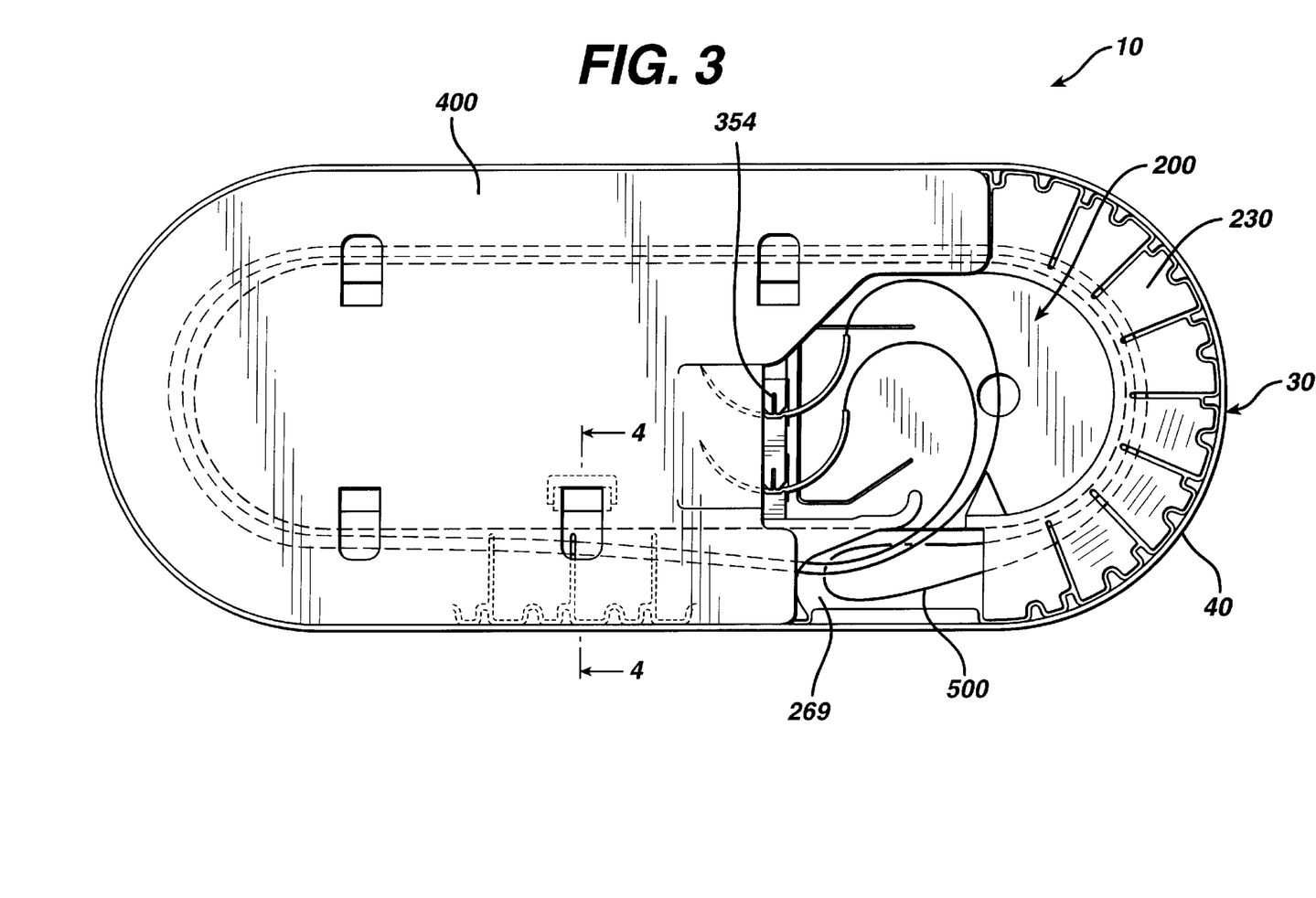
FIG. 3 is a top, plan view of the package of FIG. 1.
Figure 4:
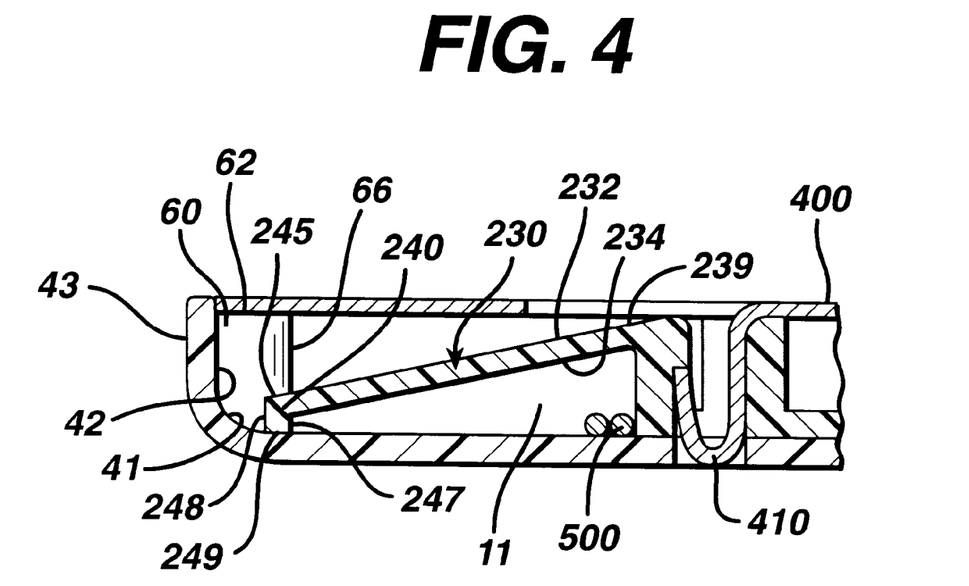
FIG. 4 is a partial cross-section taken along View Line 4—4 of the package illustrated in FIG. 3.
Figure 5:
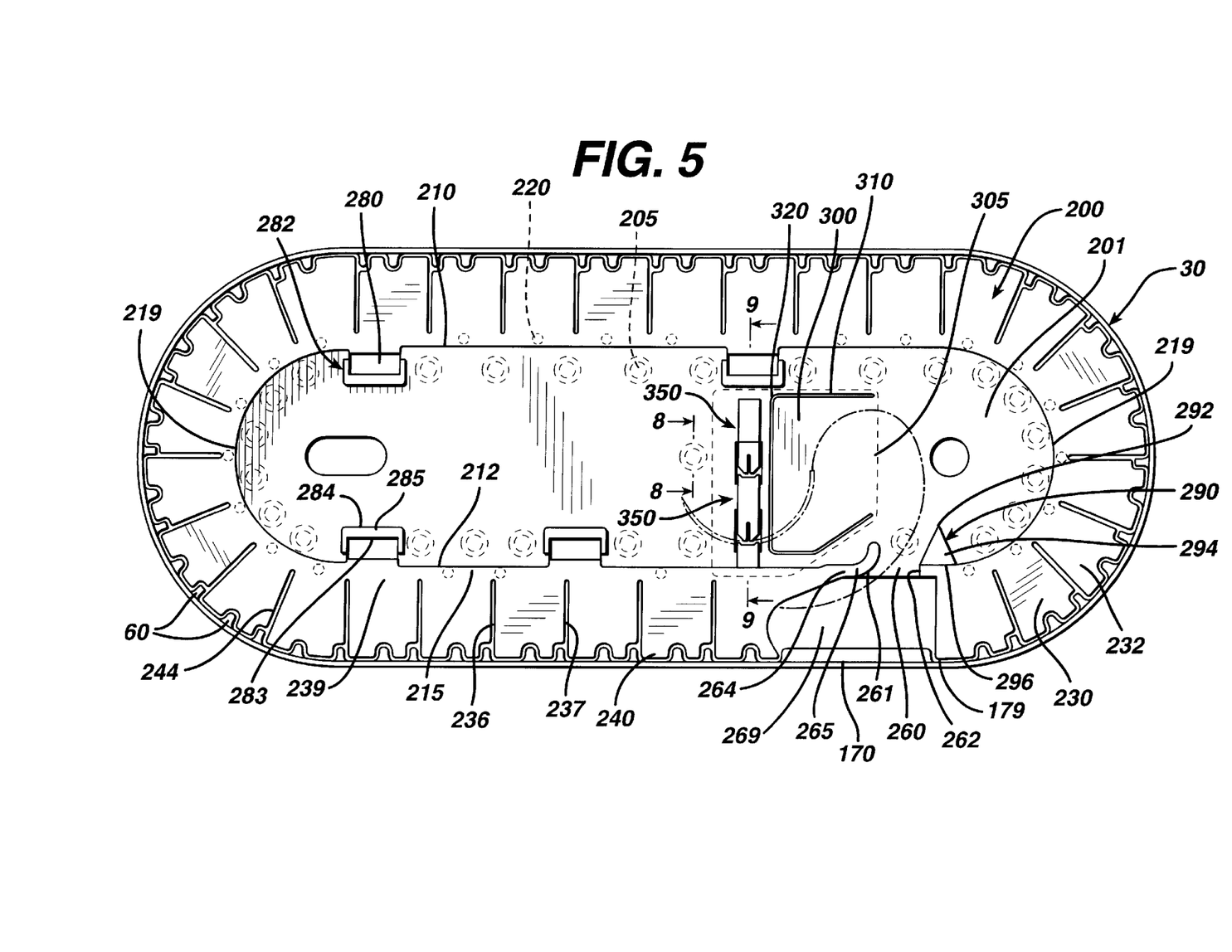
FIG. 5 is a top, plan view of a package of the present invention having a single needle and suture packaged therein; the package is seen without a paper cover mounted thereto.
Figure 7A:
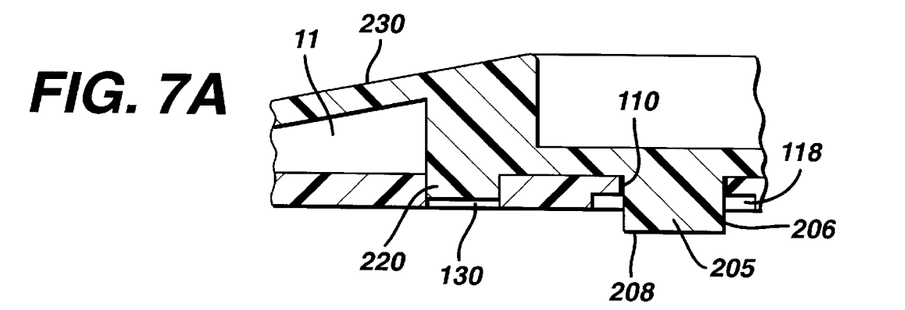
FIG. 7A is a partial cross-sectional view taken along View Line 7A—7A of the package of FIG. 6 illustrating a rivet mounted in a rivet receiving hole and a pin mounted in a pin receiving hole prior to the flattening of the bottom section of the rivet.
Figure 7B:
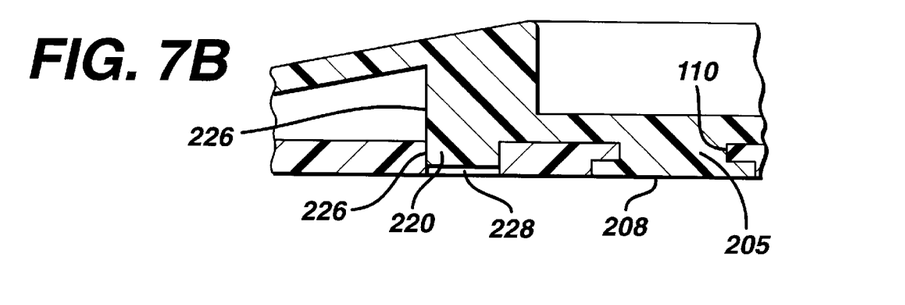
FIG. 7B is a cross-sectional view of the package of FIG. 6 taken along View Line 7B—7B showing the bottom portion of the rivet flattened into the annular space surrounding the rivet receiving hole.
Figure 8:
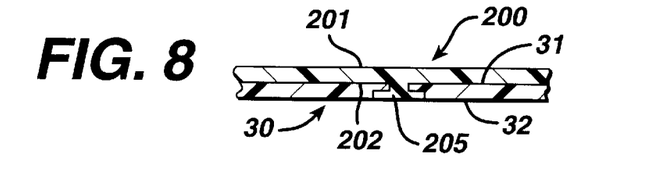
FIG. 8 is a partial cross-sectional view taken along View Line 8—8 of FIG. 5 illustrating the top member riveted to the base member.
Figure 9:
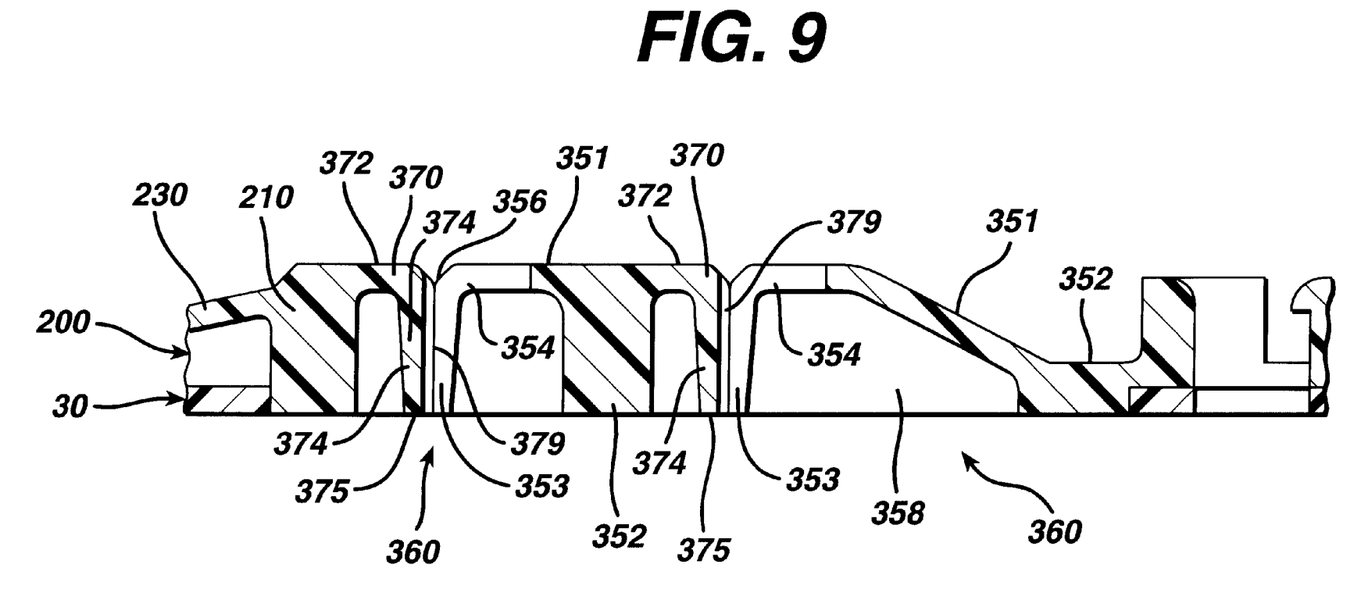
FIG. 9 is a cross-sectional view of the package of FIG. 5 taken along View Line 9—9 illustrating the needle park members.
Figure 11:
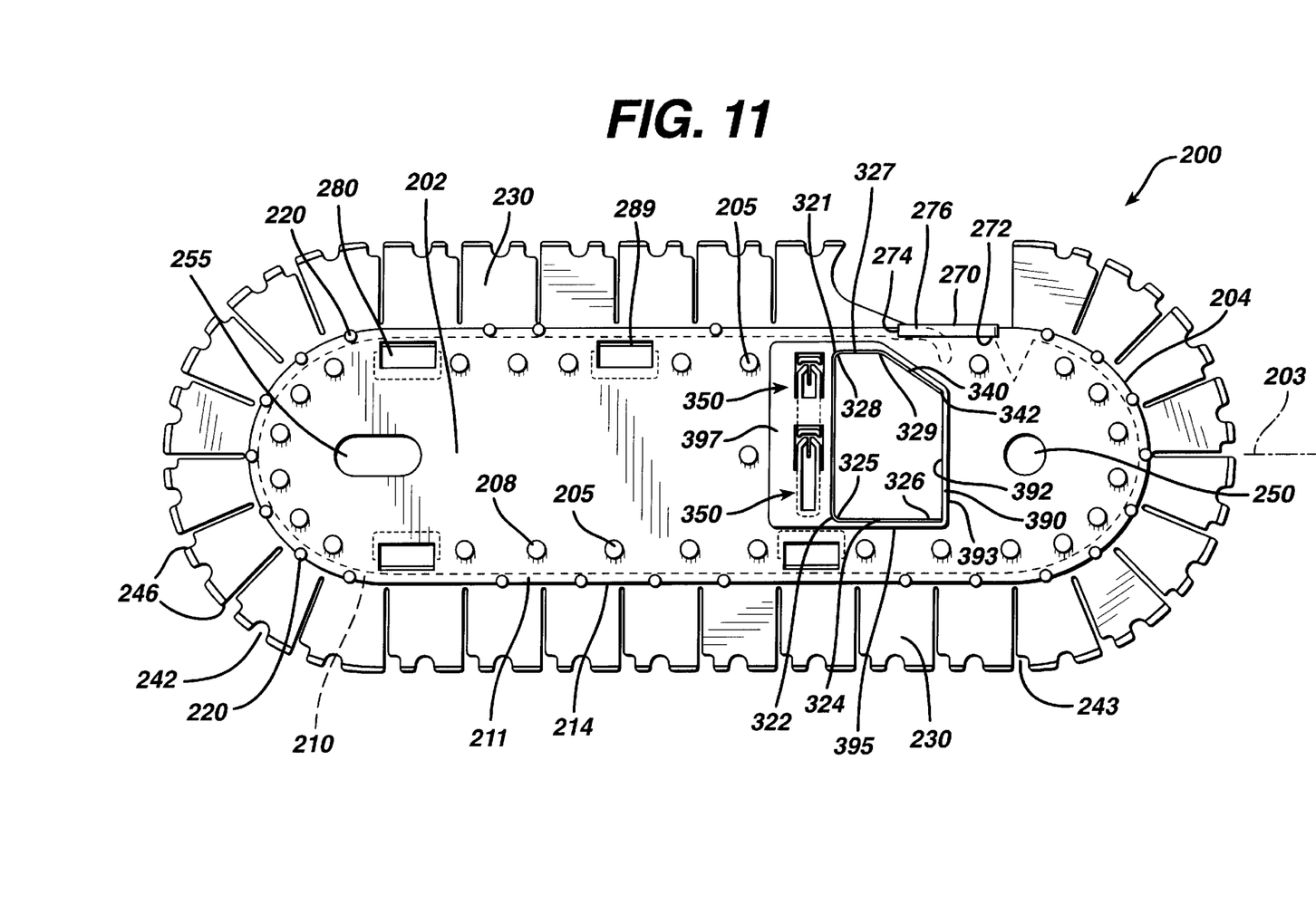
FIG. 11 is a bottom view of the channel cover member of the present invention.

Referring now to FIGS. 1, 5 and 11, the suture channel cover 200 is seen to be illustrated. The suture channel cover 200 has top side 201, bottom side 202, and periphery 204. Cover 200 is also seen to have longitudinal axis 203. Extending downwardly from the bottom 202 of the channel cover member 200, as seen in FIG. 11, are the rivets 205. Rivets 205 are seen to have sides 206 and bottoms 208. The rivets 205 are preferably circular in cross-section, but may have other geometrical cross-sections including oval, square, polygonal, and the like and equivalents thereof. Although not preferred, rivets 205 may be replaced by other conventional fastening devices including locking pins, screws, etc. The holes 110 would be changed accordingly to adapt to any such different fasteners. Also extending downwardly from bottom 202 are the locating pins 220 as seen in FIG. 7B. Locating pins 220 are seen to have bottoms 228 and sides 226. Pins 220 preferably have a cylindrical configuration but may have other geometric shapes as well. Referring now to FIG. 5, seen to extend upwardly from the top 201 of the cover 200 about the periphery 204 is the peripheral track wall 210. Track wall 210 is seen to have inner side 212, outer side 214, bottom 211 and top 215 and opposed ends 219. It is preferred that the sides 226 of pins 220 extend partially out from outer side 214 on the opposed curved end sections of track wall 200. Optionally, the sides 226 of pins 220 may extend partially out from the inners side of track wall 210 adjacent to ends 219.

Extending outwardly from the track wall 210 are the cover door members 230. It is preferred that the cover members 230 extend out from the top 215 of wall 210, but may also extend from the side 214. The cover members 230 are seen to have tops 232, bottoms 234, opposed sides 236 and 237, outer free ends 240 and hinged ends 239. Preferably, the hinged end 239 has a "living hinge" configuration wherein the door is cantilevered. The door members 230 are angulated with respect to inner track wall 210 such that the ends 240 of the door members 230 are located in the resting state below the bottom 202 of the cover 200 prior to assembly of package 10. Each cover member is seen to be separated by a space 244. The cover members are further seen to have an outer end 240, a central notch 242 and an offset notch 243 adjacent to one side. The central notch 242 is seen to be semi-circular in shape although other geometric configurations can be used. The notch 243 is seen to extend into outer end 240 and the outer end of the side 237. Notch 243 is seen to be a substantially rectangularly shaped opening having curved corners, although other geometric configurations may be used. Extending downward from the end 240 of cover member 230, is the downward rim 245. Downward rim 245 is seen to have inner side 247, outer side 248 and bottom 249 and ends 246. As mentioned above, although it is preferred that hinged ends 239 extend from track wall 210 in a manner to form a "living hinge", cover members 230 may also be connected or mounted to wall 210 using other conventional hinges and attachment methods.

The pin winding holes 250 and 255 are seen to be contained at opposite ends of the cover member 200. Winding pin holes 250 and 255 are seen to extend through member 200 and to be disposed in cover member 200 along longitudinal axis 203, toward either end, and are further seen to line up with winding holes 120 and 125 in base member 30. Winding pin hole 250 is seen to be circular in shape, while winding pin hole 255 is seen to be oval. However, other geometric shapes can be utilized. The suture exit port 260 is seen to be contained in track wall 210. Exit port 260 is seen to have ends 261 and 262. Adjacent to port 260 is the track opening 269. The curved arm 264 having inwardly curved end 265 is seen to extend up from top side 201 beginning at inner wall 210 adjacent to end 261 of port 260. Extending downward from the bottom side 202 of cover member 200 next to the port 260 is the port tab member 270. Tab member 270 is seen to have opposed longitudinal sides 272, opposed ends 274, and bottom 276. Tab member 270 is in alignment with rectangular port tab opening 160 in base member 130. Also seen to extend through the cover member 200 are the cover tab mounting holes 280. Each tab mounting hole 280 is seen to be surrounded on three sides by wall 282 extending up from side 201 of cover 200. Wall 280 is seen to have inner side 283, outer side 284 and top 285. Cleat member 289 is seen to extend down from the bottom 202 of member 200, adjacent to opening 280 and beneath track wall 210. Adjacent to end 262 of the port 260 and extending up from top side 202 is ramp member 290. Ramp member 290 is seen to preferably have a conically shaped configuration with apex 292 and curved top surface 294 and end 296, however other ramp configurations may be utilized. The lifting tab 300 is seen to be formed in base member 30 by the slit 310. Slit 310 is seen to have section 320 which is substantially perpendicular to the longitudinal axis 203 of cover member 200. Slit section 320 is seen to have ends 321 and 322. Intersecting section 320 at ends 321 and 322, respectively, and perpendicular thereto, are the side slit sections 324 and 327 having ends 325 and 326, and ends 328 and 329, respectively. Intersecting the end 329 of slit 327 is the angulated slit 340 having end 342. Between the ends 342 of slot 340 and end 326 of slot 324 is the living hinge member 305. Living hinge member 305 permits the lifting tab 300 to rotate about the hinge 305 and down into opening 150 in base member 30. An equivalent conventional hinge can be used in place of a living hinge, although not preferred, and other conventional ways of mounting the tab 300 to cover member 200 may also be utilized. Adjacent to the tab 300 are the needle park members 350. Members 350 are seen to have hinged arms 351 having first end 352 fixed to top 201 of cover member 200 and having opposite free end 353, which is divided by slot 354. Arm 351 can deflect or rotate about fixed end 352 into opening 360. The free end 352 is seen to be angulated from a top perspective to an edge 356. Each member 350 is seen to have cavity 358. Extending through member 200 below each free end 353 are the park openings 360. Adjacent to each free end 353 of the park members 350 are the cantilevered retention arms 370. The retention arms 370 are "L-shaped" members having smaller fixed legs 372 and longer movable legs 374. Movable legs 374 have ends 375 which may extend into park openings 360. Free ends 353 and legs 374 are separated by spaces 379. Extending downward from bottom 202 of member 200 about the periphery of slit 310 and also about openings 360 is the spacer wall 390 having inner side 392, outer side 393 and bottom 395. The spacer wall has thicker section 397 adjacent to openings 360.

The packages 10 of the present invention are assembled in the following manner. Base member 30 is aligned with cover member 200 such that the rivets 205 are in alignment with the rivet receiving holes 110, and locating pins 220 are in alignment with openings 130. Also, winding pin openings 255 and 250 are aligned with openings 125 and 120 respectively. Then, cover 200 is mounted to base member 30 such that the rivets 205 are inserted into and through the holes 110 and locating pins 220 are inserted through holes 130, and tab 290 is contained within opening 160. When this is accomplished, the standoff members 60 are contained within the notches 242 and 243 of door members 230. In addition, the spacer wall 390 is contained within opening 150. Then as seen in FIG. 6, 7, 8 and 9, the ends 208 of the rivets 205 are spread by using conventional techniques such as heating, ultrasonic treatments, and the like such that the cover 200 is firmly affixed to the base member 30, and the riveted or spread ends 208 are contained within annular openings 118. At this stage, the bottom 202 of cover member 200 is substantially in contact with the top 31 of the base member. When package 10 is thusly assembled, a suture channel 11 is formed consisting of the inner sides 247 of the rims 245 of the cover door members 230, the surfaces 66 and 68 of the standoff members 60, the top side 31 of member 30, and the outer side 214 of track wall 210. The channel 11 is covered by the cover members 230. When assembled, the bottoms 249 of cleats 245 are seen to be resting at least in part on top 31 of member 30, and the bottom 249 typically has at least some downward bias against top side 31.

In order to mount sutures 500 having surgical needles 550 mounted to one end 502 in the package 10, the assembled package 10 is mounted into a conventional, rotatable winding fixture, such that the winding pins of the winding fixture are inserted through the winding pin openings 125 and 130 and 255 and 250. Needle 550 is placed into needle park members 350. Then, the suture is threaded out of port 260 into the channel 11. Next, the suture 500 is guided into the channel 11 by a conventional stylus which lifts the cover door members 230 as the package 10 is rotated in the fixture such that the suture is completely wound in the channel 11 as the package is rotated. This may be repeated with additional sutures 500 and needles 550. If desired, a cover member 400 may be mounted to the package containing the wound suture. Cover member 400 is seen to have base member 405 and downwardly extending cleat members 410. Cleat members 410 are inserted through openings 280. The bottom 415 of the cleat member 410 is retained by the cleat retention member 289. The bottom 401 of cover member 40 rests upon the top surfaces 62 of standoff members 60. The package 10 containing the sutures 500 and needles 550 may then be placed in a conventional pouch or package for conventional sterilization treatments such as gaseous sterilants, autoclaving, radiation and the like. When used by the physician in a surgical procedure, the package 10 is placed into a sterile field. Using a conventional needle grasper, the surgeon pushes down lifting tab 300 partially into opening 150 and the needle 550 is grasped and removed from the needle park members 350. The needle 550 and suture 500 are then pulled away from the package 10 and suture 500 exits through exit port 260 and channel exit 269, and then from channel 11.

The packages of the present invention may be manufactured from conventional moldable materials. It is especially preferred to use polyolefin materials such as polyethylene and polypropylene, other thermoplastic materials, and polyester materials such as nylon, and equivalents thereof. Preferably the packages of the present invention are injection molded, however, the packages may be formed by other conventional processes and equivalents thereof including thermo-forming. If desired, the packages may be manufactured as individual assemblies or components which are then assembled.

The sutures and needles that can be packaged in the packages 10 of the present invention include conventional surgical needles and conventional bioabsorbable and non-absorbable surgical sutures and equivalents thereof. The packages of the present invention are useful to package small diameter sutures which were previously difficult to package in tray packages because of removal or hang-up problems upon withdrawal of such suture from the packages. These problems have been overcome using the packages of the present invention.

Although this invention has been shown and described with respect to detailed embodiments thereof, it will be understood by those skilled in the art the various changes in form and detail thereof may be made without departing from the spirit and scope of the claimed invention.

We claim:
1. A package for surgical sutures, comprising:
    a base member having a top, a bottom and an outer periphery and a longitudinal axis;
    an outer wall extending upwardly from the periphery of said base member, said outer wall having an inner surface, an outer surface, and a top;
    a plurality of standoff members extending radially inward from the inner surface of the outer wall onto at least part of the top surface of the base member, each standoff member having a top, a bottom and an outer surface;
    a plurality of fastener receiving holes extending through the base member;
    a plurality of locating pin receiving holes extending through the base member;
    a lifting tab receiving opening extending through the base member;
    a suture channel cover member having a top surface, a bottom surface and an outer periphery;
    a plurality of fastener members extending downwardly from the bottom of the cover member;
    a plurality of locating pin members extending downwardly from the bottom surface of the cover member;
    an inner track wall extending upwardly from the outer periphery of the cover member, said inner track wall having an inner side, an outer side and a top;
    a plurality of cantilevered cover door members extending radially outward from the inner track wall, each door member having a top surface, a bottom surface, an inner end and an outer end, and sides, said door members having a centrally located notched opening in the outer end extending partially into the door member, said door members separated by spaces, wherein said door members are angulated with respect to the inner track wall;
    a rim member extending downwardly from the outer end of each door member;
    an opening in the inner track wall forming a suture port having a first end and a second end;
    a curved suture port arm adjacent to the first end of the suture port, said port arm extending upwardly from the top surface of the base member from the track wall to a point on the base member interior to the track wall;
    a port ramp member having a ramped surface adjacent to the second end of the port opening;
    a slit in the cover member forming a lifting tab;
    needle park means located interior to inner track wall and extending from the top surface of the cover member for retaining a surgical needle,
wherein the cover member is mounted to the base member such that the fasteners are received by the fastener retention holes, the locating pins are received by the pin receiving holes, and the bottom surface of the cover member is substantially adjacent to the top surface of the base member, thereby forming a suture channel between the outer surface of the inner track wall, the inner surface of the rim members, the inner surfaces of the door members and the top surface of the base member, wherein the bottoms of the rim members rest upon the top surface of the base member.

2. The package of claim 1 additionally comprising holes through the base member for receiving winding pins.

3. The package of claim 1 further comprising holes in the base member and holes in the cover member for receiving cover cleats.

4. The package of claim 1 further comprising a cover, said cover comprising a flat member and mounting cleats extending downwardly from the cover.

5. The package of claim 1 further comprising a suture wound into the winding channel and a surgical needle mounted in the needle park means.

6. The package of claim 1 wherein the fastening members are rivets.

7. The package of claim 1, wherein the rivet holes are surrounded by annular recesses.

8. The package of claim 1 wherein the door members additionally comprise a second notch in the end adjacent to on side and extending into the door member.

9. The package of claim 1 wherein the package has an oval configuration.

10. The package of claim 1 wherein the port ramp has a conical configuration.

11. The package of claim 1 wherein the fasteners are positioned interior to the locating pins and arrayed such that there is on locating pin between adjacent fasteners.

12. The package of claim 1 wherein the standoff members have a curved outer surface.

13. The package of claim 1 wherein the standoff members have a flat outer surface.

14. The package of claim 1 wherein the standoff members have alternating flat and curved surfaces.

15. The package of claim 1 wherein the needle park member comprises a pair of opposed cantilevered members having fixed and free ends separated by a gap, wherein the free ends of the cantilevered members are located over an opening in the base member.

16. The package of claim 1 wherein the inner track wall has opposed curved ends, and the winding pins adjacent to these ends extend partially out from the inner surface of the inner track wall.

* * * * *